US012788459B1

(12) United States Patent
Gitlin

(10) Patent No.: US 12,788,459 B1
(45) Date of Patent: Nov. 10, 2026

(54) WIRE TENSIONER FIXATION DEVICE

(71) Applicant: David Gitlin, Naples, FL (US)

(72) Inventor: David Gitlin, Naples, FL (US)

(73) Assignee: GITLIN LLC, Naples, FL (US)

( * ) Notice: Subject to any disclaimer, the term of this patent is extended or adjusted under 35 U.S.C. 154(b) by 0 days.

(21) Appl. No.: 18/441,033

(22) Filed: Feb. 14, 2024

Related U.S. Application Data

(60) Provisional application No. 63/446,197, filed on Feb. 16, 2023.

(51) Int. Cl.
*A61B 17/84* (2006.01)

(52) U.S. Cl.
CPC .................................. *A61B 17/842* (2013.01)

(58) Field of Classification Search
CPC ..... A61B 17/64; A61B 17/645; A61B 17/641; A61B 17/642; A61B 17/649; A61B 17/66; A61B 17/88; A61B 17/886
See application file for complete search history.

(56) References Cited

U.S. PATENT DOCUMENTS 5,496,319 A * 3/1996 Allard ................ A61B 17/6441 606/56
2015/0257788 A1* 9/2015 Jay ......................... A61B 17/62 606/56
2019/0223933 A1* 7/2019 Wigginton ......... A61B 17/6425

* cited by examiner

*Primary Examiner* — Christopher J Beccia

(57) ABSTRACT

A bone-fixation wire extending across an external bone fixator, such as a ring, is tensioned by a wire tensioner fixation device that includes a rotator that is rotatable to a rotated position. In some embodiments the rotator is rotatable around a hub that is part of a mount that is adapted to be affixed to the external bone fixator. In some embodiments the rotator includes at least one wire-engaging element that enables the rotator to grasp and secure the bone-fixation wire so that the rotation tensions the bone-fixation wire. In some embodiments the rotator and/or the mount are so arranged as to enable the rotator to be secured at the rotated position.

25 Claims, 12 Drawing Sheets

WIRE TENSIONER FIXATION DEVICE

CROSS-REFERENCE TO RELATED APPLICATION

This application claims the benefit of provisional patent application 63/446,197 received Feb. 16, 2023.

FIELD OF THE INVENTION

The invention relates generally to medical devices for use in the surgical fixation of a patient's bone, and more particularly, to wire tensioning systems for external ring bone-fixation and methods for using the same.

BACKGROUND OF THE INVENTION

External fixation systems are used for surgical stabilization during surgical care of the extremities in order to, for example, treat fractures of bone as well as to realign bone segments in cases of deformity correction or orthopedic trauma. Such systems include a ring or ring segments—referred to as fixators—and flexible Kirshner-type bone-fixation wires. The wires come in many diameters (e.g., from 1.5 mm to 2 mm) and are usually made from surgical stainless steel. They are driven through the bone fragments with sharp points at the ends of the wires using a wire driver tool. The wires are then attached to the rings using a wire fixation bolt. The wires themselves are flexible because of their thin diameter.

FIG. 1 shows an external fixation system applied to a lower leg/foot with just the bones thereof being depicted. The system illustratively includes three fixators—two complete rings 12 and one U-shaped ring segment 13. Kirshner-type wires 14 passing through the bones are anchored at opposing points of the various fixators.

In order for the surgeon to create a stable fixation construct, which is essential in proper bone healing fixation, the wires need to be tensioned.

There are a number of ways to tension the wires. A common way is shown in FIG. 2. The process of tensioning begins with driving a wire 14 through a bone (not shown). Then the wire is clamped at the distal end using a wire fixation bolt 18 which simply attaches the wire at one end of the ring. The other end of the wire is placed into another wire fixation bolt 16 on the opposite side of the ring. Wire tensioning tool 11 is introduced, placed onto the wire through a cannulated portal in the tool and then the tool is activated in order to tension the wire.

There are a number of wire tensioners on the market but the mechanism of action of all of them is essentially the same: the tensioner first grasps the wire and then pulls on the wire to tension it. Since the wire is attached on the opposite, distal, end with a tightened wire fixation bolt the wire is actually stretched until it has so much tension that it is no longer as flexible as it was in its untensioned form. This tensioning of the wire creates a very solid bone-fixation construct. At this time, the bolt 16 is tightened with the normal technique using a wrench and the wire tensioner is removed. The wire is now tensioned. The wire fixation bolts on either side of the ring maintain the tension on the wire after the wire tensioner is removed.

Each tensioner is graduated and marked in newtons or pounds of force of tension. The wires are tensioned to a preset tension level as needed.

Another method of tensioning a wire does not use a wire tensioner tool. This is referred to as the Russian tensioning, as illustrated in FIG. 3. In this technique, using wrenches 13, wire fixation bolt 11 is used as a pulley and the wire 14 is forcefully turned around the pulley against the other end that was attached to the ring similarly to the first technique above. This forceful pulley induces a tensioning force onto the wire. Since there are no gradations or markings to refer to in this technique, the surgeon uses general guidelines in as how far to pulley the wire around the bolt. Degrees of pulley can be likened to the pounds of tension applied when using a marked tensioner.

Currently the technique of using the wire tensioner is cumbersome and adds considerable time and technique to the surgical case. To be able to achieve both the attachment of the wire to the ring and tighten the wire fixation bolt to that same ring, and to apply the wire tensioner, to tension and then tighten the opposite bolt takes a significant number of steps.

Thus, it is desirable to improve the wire tensioning of external fixation systems.

SUMMARY OF THE INVENTION

A bone-fixation wire extending across a fixator, such as a ring fixator, is tensioned by a wire tensioner fixation device embodying the principles of the invention. In illustrative embodiments, the wire tensioner fixation device—referred to hereinafter as the "wire fixation device"—includes a rotator rotatable around a hub. The hub is part of a mount that is adapted to be affixed to the fixator and the rotator is rotatable around the hub. In direct contradistinction to the above-described Russian tensioning, the rotation is in a direction substantially non-paralleling the plane of the fixator. The rotator is able to secure the wire in or on the rotator so that the rotation tensions the bone-fixation wire. The rotator and/or the mount are so arranged as to enable the rotator to be secured at the rotated position.

The present invention further comprises methods of tensioning a bone-fixation wire, wherein the tensioning is carried out using the inventive wire fixation device.

This Summary of the Invention is presented herein to help the reader understand the invention and is neither intended to be, nor should it be construed as being, representative of the full extent, scope or breadth of the invention. In particular, then, no limitation as to the full extent, scope or breadth of the invention is intended by either the inclusion or non-inclusion in this Summary of the Invention of any particular elements, components, functions, characterizations or the like.

BRIEF DESCRIPTION OF THE DRAWING

The figures in the drawing are not necessarily to scale. In certain instances, details that are not necessary for an understanding of the disclosure may have been omitted.

DETAILED DESCRIPTION OF EMBODIMENTS OF THE INVENTION

Figure 1:
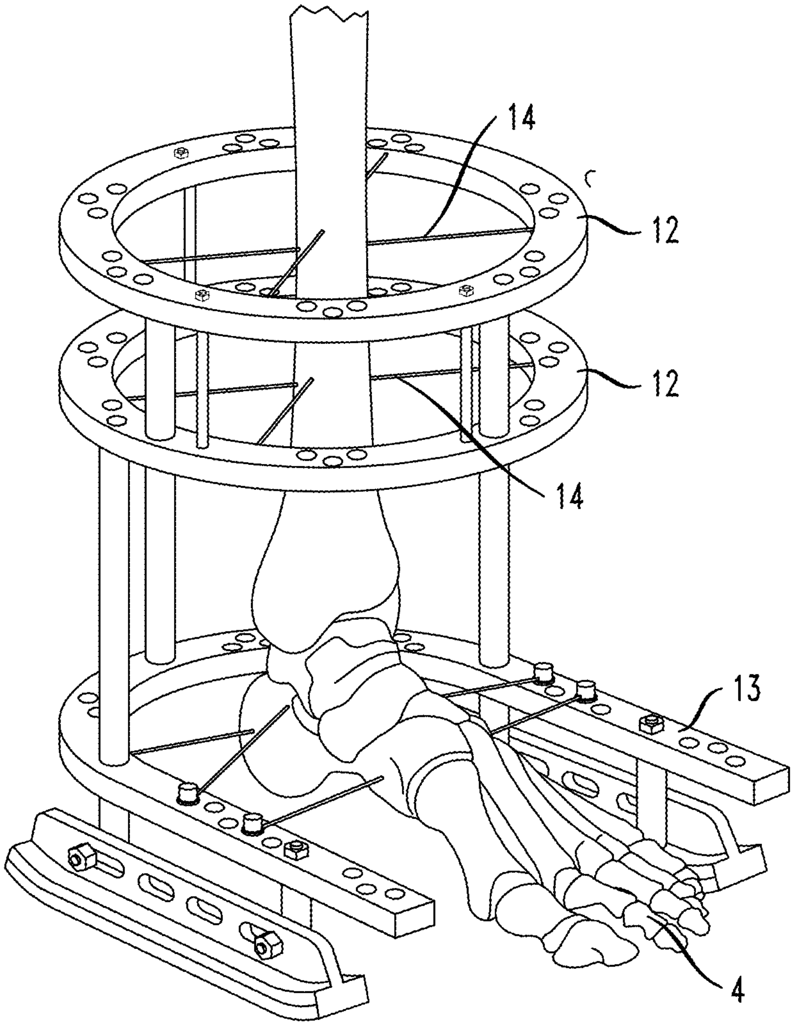
FIG. 1 PRIOR ART
FIGS. 1-3 illustrate the state of the prior art relevant to the invention.
Figure 2:
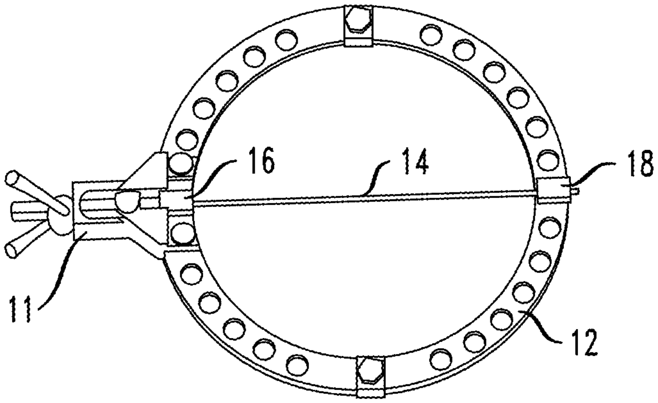
FIG. 2 PRIOR ART
Figure 3:
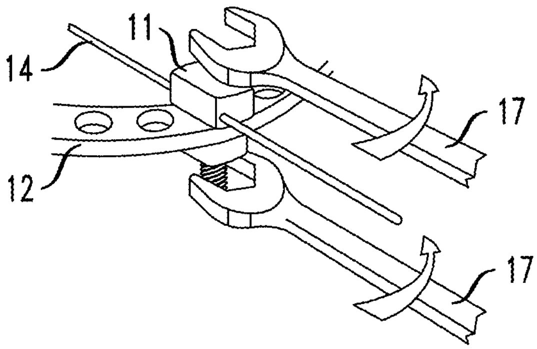
FIG. 3 PRIOR ART
Figures 4A, 4B, 4C, 4D, 4E:
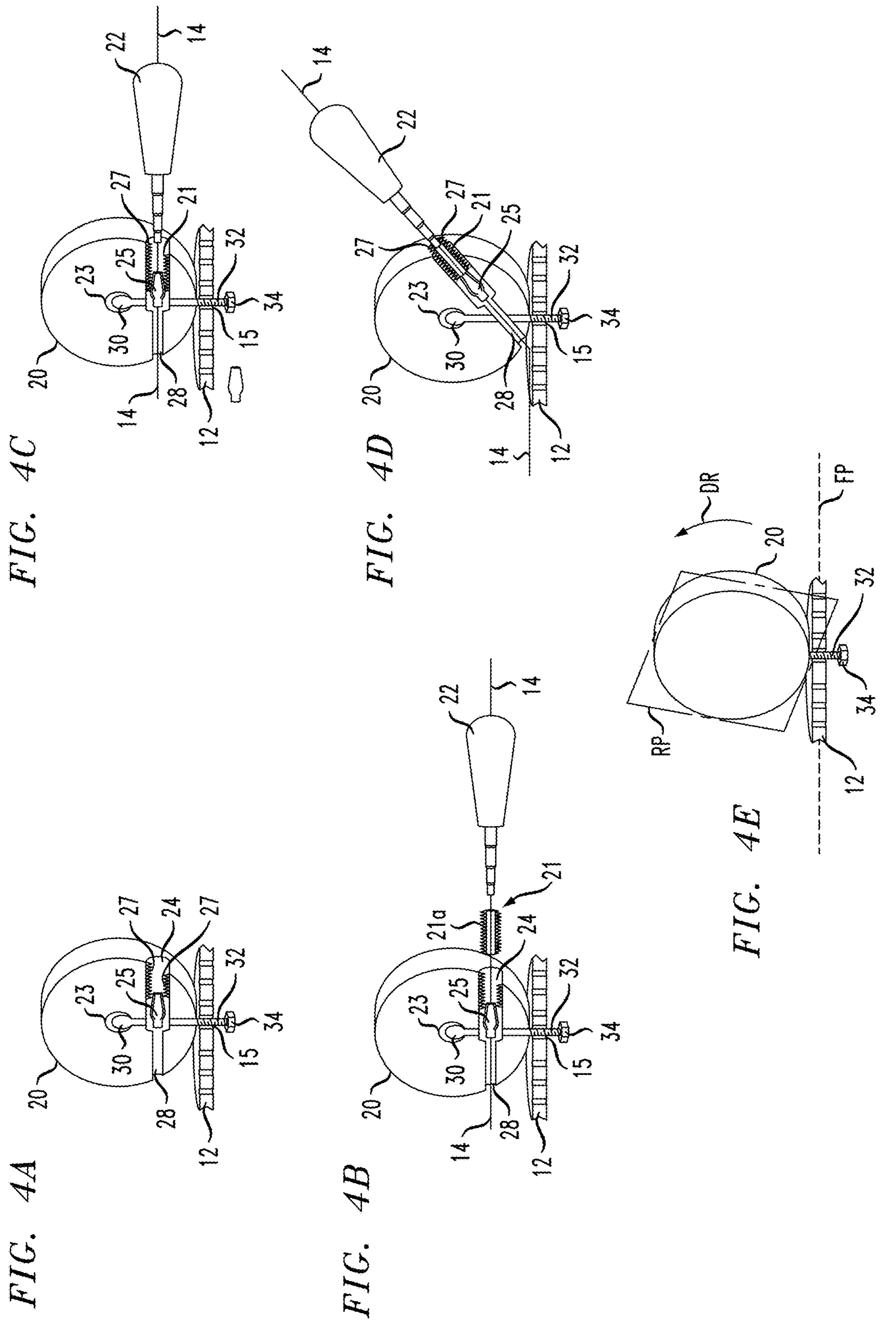
FIGS. 4A-4D are partial cross-sectional perspective views of an illustrative wire fixation device embodying the principles of the invention, the various views depicting the wire fixation device at different stages of a method performed by a surgeon using the wire fixation device to tension and secure a bone-fixation wire onto a fixator.
FIG. 4E is a simplified drawing of the embodiment of FIGS. 4A-4D illustrating that the rotator of the wire fixation device is rotatable in a direction substantially non-paralleling a plane of the external bone fixator.

FIGS. 4A-4D are cross-sectional perspective views of an illustrative wire fixation device embodying the principles of the invention, the various views depicting the wire fixation device at different stages of a method performed by a surgeon using the wire fixation device to tension and secure a bone-fixation wire onto a fixator;

With reference first to FIG. 4A, it can be seen that the wire fixation device comprises a generally disc-like rotator 20 having a substantially circular profile. Rotator 20 is mounted on an external bone fixator—hereinafter fixator—12 which is illustratively a ring or ring segment with holes. A hub 30 extends through a hole 23 in rotator 20 so that rotator 20 is rotatable around hub 30 in a direction non-paralleling the plane of fixator 12. This is in contrast to, for example, to the so-called Russian tensioning prior art discussed above in which a wire fixation bolt rotates in a plane that is substantially parallel to the plane of the fixator.

Hub 30 is part of a mount that comprises hub 30, mounting post 32 and nut 34. Hub 30 is substantially centered on rotator 20. Mounting post 32 is adapted to be secured to fixator 12 at the point in time that the wire fixation device is being put in place on fixator 12. In particular, mounting post 32 is dimensioned so as to able to be passed through one of the holes—hole 15—in fixator 12. Mounting post 32 has external threads that engage with the internal threads of nut 34. As shown in FIG. 4A, nut 34 is not initially tightened against fixator 12.

Rotator 20 may be held in place on hub 30 in any convenient manner, such as by a nut screwed onto hub 30, which would be threaded at least at its free end so as to accept the nut. Although not explicitly shown in FIGS. 4A-4D, such an arrangement is shown explicitly in FIG. 11 in connection with the embodiment shown in that FIG. and this manner of securing the rotator to the hub can be used in any of the embodiments disclosed herein unless a different way of doing this is explicitly disclosed as, for example, in the embodiment of FIG. 13. Another possibility for securing the rotator to the hub could be to have the end of the hub that extends beyond the surface of the rotator to be flared or flanged so as to prevent the rotator from becoming displaced off the hub.

Figure 6A:
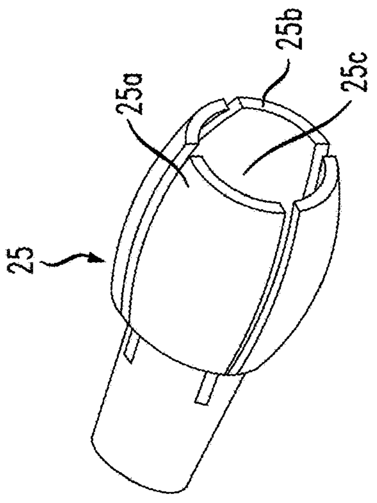
FIGS. 6A-6B are perspective and end views, respectively, of the collet.
Figure 6B:
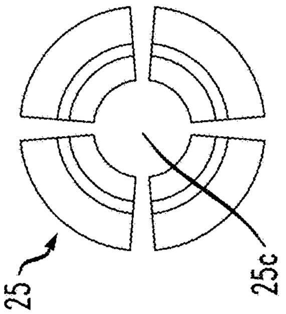

Referring back to FIG. 4A, it can be seen that extending transversely through rotator 20 is a channel having a first channel section 28 and a wider channel section 24. For convenience those two sections of the channel will be referred to as channels 28 and 24, even though they are actually sections of a single channel extending through rotator 20. Channel 28 is sufficiently wide to accept a fixation wire 14 that will have been previously secured to fixator 12 at a location that is substantially opposite from hole 15. Channel 24 is wider than channel 28 and has disposed therein a wire-engaging element 25 that is illustratively a collet, which is a collar or tube that is slotted at one end so as to create a plurality of fingers 25*a*. Collet 25 is shown in greater detail in FIGS. 6A and 6B as being divided at one end into four fingers 25*a* separated by slots 25*b* and surrounding an opening 25*c* extending through collet 25.

Figure 7A:
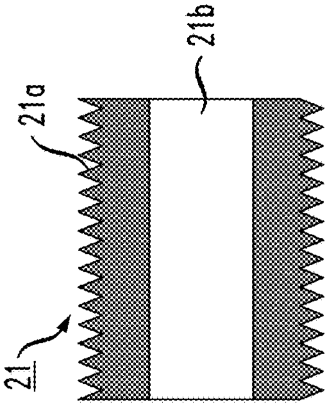
FIGS. 7A-7B are cross-sectional and end views, respectively, of a cannulated nut engageable with the leafs of the collect in such a way as to cause the collet to securely grasp and secure the bone-fixation wire.
Figure 7B:
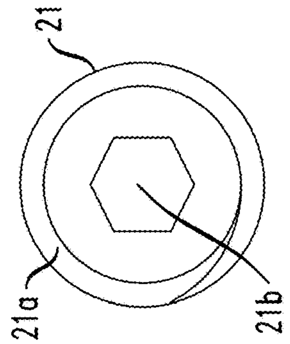

FIG. 4B shows the wire fixation device with a fixation wire 14 now having been passed through channel 28 and collet 25 and out the end of channel 24. Wire 14 is further passed through a cannulated nut 21 that, at this point, is outside of the wire fixation device. Wire 14 is further passed through a hexagonal-tip cannulated screwdriver 22. As shown in FIGS. 7A and 7B, nut 21 has external threads 21*a* and an interior cannula 21*b*. Although not explicitly shown in the FIG., cannula 21*b* is cylindrical except for a short hexagonal section at one end that enables screwdriver 22 to engage with nut 21 and to turn it. Referring back to FIG. 4A, it can be seen that the wall of channel 24 has threads 27 and, as shown in FIG. 4C, nut 21 has now been screwed into channel 24 wherein the external threads 21*a* of nut 21 engage with the threads 27 on the wall of channel 24. This operation has illustratively been carried by inserting nut 21 into the mouth of channel 24 and then using screwdriver 22 to screw nut 21 into channel 24. Collet 25 is tapered to make room for threads 27 to extend inwardly into channel 24 beyond the end of collect 25. In addition, the diameter of cannula 21*b* is such as to be able to accept the fingers 25*a* of collet 25 into cannula 21*b* as nut 21 is screwed further into channel 24 by screwdriver 22. As a result, nut 21 engages with fingers 25*a* of collet 25 as the nut travels inwardly into channel 24 upon being screwed into place. Specifically, nut 21 squeezes fingers 25*a* closer and closer together, that is, increasingly inwardly toward the center of opening 25*c* as the nut travels increasingly into channel 24. Ultimately fingers 25*a* grasp and secure wire 14, as the result of which wire 14 is held securely in a fixed position vis-à-vis rotator 20, thereby enabling wire 14 to be tensioned when rotator 20 is rotated as discussed below.

Figure 5:
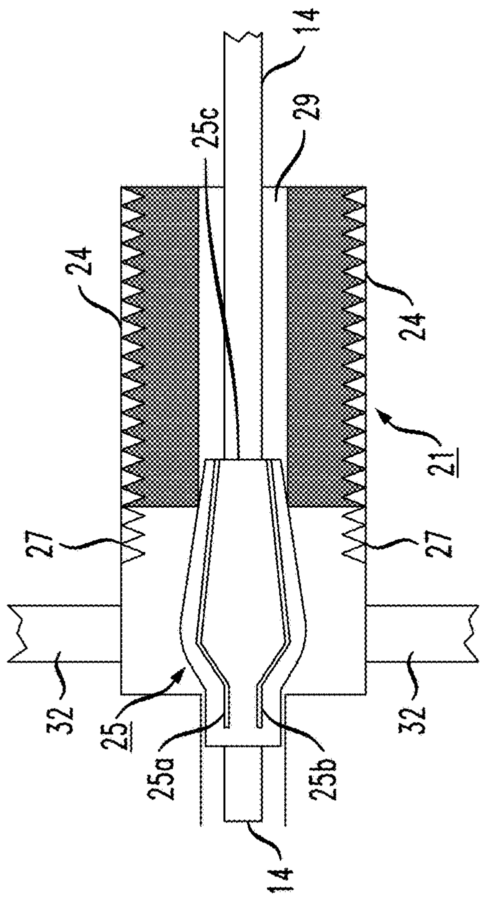
FIG. 5 is a detailed view of the channel that extends through the wire fixation device of FIGS. 4A-4D, there being disposed within the channel a collet for securing the wire within the rotator.

FIG. 5 is a detailed view of nut 21 within channel 24 shown at a point in time prior to that depicted in FIG. 4C, at which time nut 21 has been partially screwed into channel 24 and has begun to engage with fingers 25*a* but has not yet fully reached the end of its travel into channel 24.

Collet 25 is not necessarily shown to scale in the FIGS. Collet 25 is to be dimensioned such that the opening 25*c* defined by fingers 25*a* is slightly larger than the fixation wire that will ultimately be passed through opening 25*c*. Importantly, collet 25 is dimensioned such that when its fingers 25*a* are squeezed together by cannulated nut 21 as described above, fingers 25*a* securely grasp wire 14 and, to repeat what was said just above, wire 14 is thereby grabbed and held securely in a fixed position vis-à-vis rotator 20, with the result that wire 14 will be tensioned when rotator 20 is rotated as discussed below.

In some embodiments opening 25*c* may have a slightly larger width than the largest fixation wire contemplated to be used for operative procedures using the wire fixation device. This will enable the wire fixation device to accept not only a fixation wire of that largest diameter but also fixation wires with smaller diameters. However in various different embodiments of the wire fixation device, opening 25*c* of the collet being used can have a range of widths that are just slightly larger than the diameters of respective different wires that might be used. This may make it easier to have collets that can tightly grasp whatever diameter wire is being tightened. In any of these cases, the interior of fingers 25*a* can be serrated or be otherwise non-smooth in order to grasp wire 14 even more firmly.

FIG. 4D shows the wire fixation device with rotator 20 having now been rotated counter-clockwise—illustratively accomplished in response to a generally upward force applied by the surgeon to still-in-place screwdriver 22 now serving as a tensioning lever. The rotation of rotator 20 to the rotated position shown in FIG. 4D tensions wire 14 as desired. At this time, and with upward force still being applied to screwdriver 22 by the surgeon, nut 34 on mounting post 32 is screwed tight against the underside of fixator 12, thereby holding rotator 20 in place and thereby maintaining wire 14 in a tensioned state. Screwdriver 22 can thereupon be removed and any excess of wire 14 can be trimmed off.

FIG. 4E is a simplified drawing of the embodiment of FIGS. 4A-4D showing the direction of rotation DR of rotator 20 as being within plane RP of the rotator and illustrating that that direction of rotation as substantially non-paralleling the plane FP of the external bone fixator;

FIGS. 8A-8D are cross-sectional perspective views of another illustrative wire fixation device embodying the principles of the invention, the various views depicting the wire fixation device at different stages of a method performed by a surgeon using the wire fixation device to tension and secure a bone-fixation wire onto a fixator;

The elements of this embodiment correspond generally to those in the embodiment of FIGS. 4A-4D and thus comprise rotator 60; channel 68; channel 69 having within it collet 25 and having threads 67 on the channel wall; a mount comprising hub 30, threaded mounting post 32 that will be extended through hole 15 of fixator 12 when the wire fixation device is being put in place on fixator 12, and nut 34 threaded onto mounting post 32. Hub 30 extends through hole 63 in rotator 60, whereby rotator 60 is rotatable around hub 30.

Figure 8C:
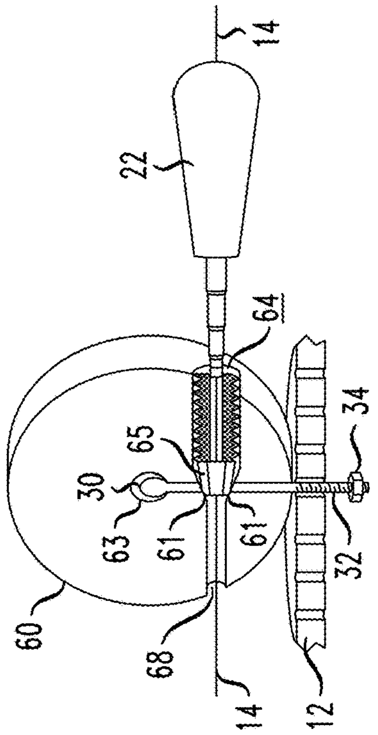
FIGS. 8A-8D are partial cross-sectional perspective views of another illustrative wire fixation device embodying the principles of the invention, the various views depicting the wire fixation device at different stages of a method performed by a surgeon using the wire fixation device to tension and secure a bone-fixation wire onto a fixator.
Figure 8D:
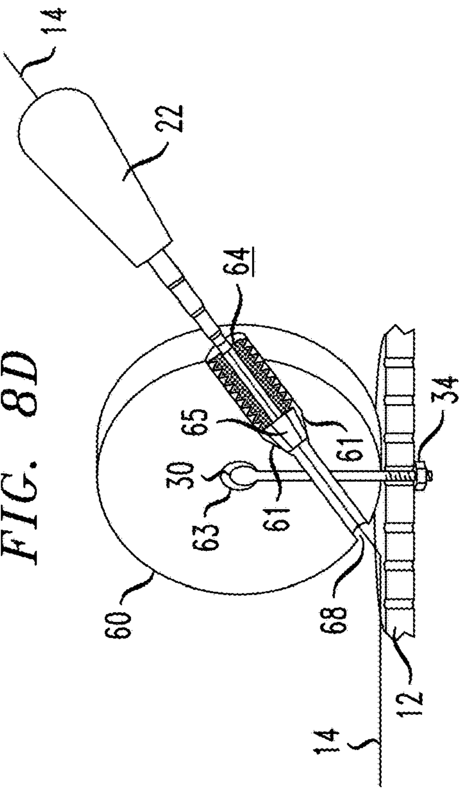
Figure 8A:
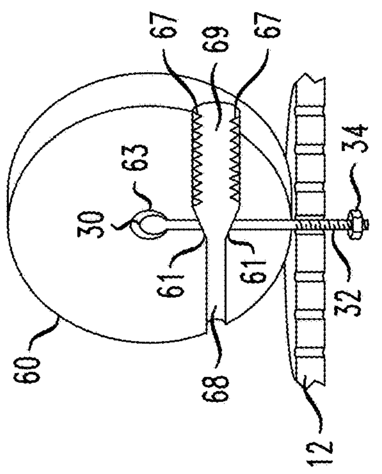
Figure 8B:
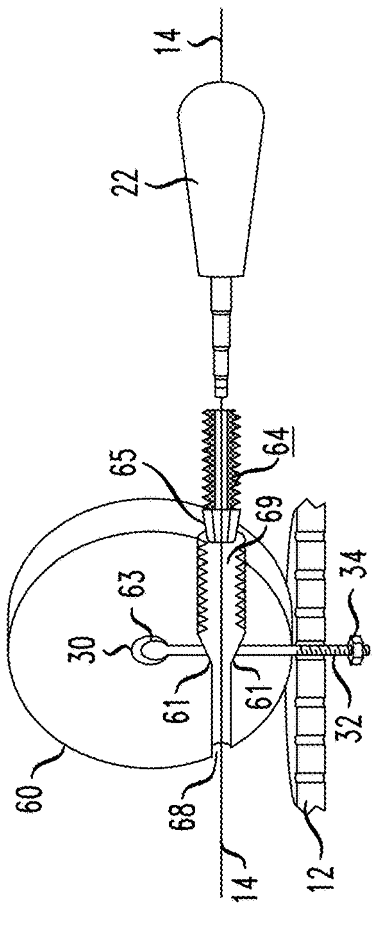

A principal difference here is the manner in which wire 14 is secured within rotator 60. Instead of cannulated nut 21, this embodiment uses a cannulated nut 64 which has a front-end collet 65. As nut 64 is screwed into channel 69 by screwdriver 22 and approaches the interior end of channel 69, collet 65 engages with cone-shaped end wall 61 of the channel. This increasingly squeezes the leafs of the collet inward until the collet is fully engaged with end wall 61, thereby grabbing wire 14 and securing it within rotator 60, as seen in FIG. 8C. Rotator is then rotated to its rotated position, as seen in FIG. 8D, and nut 34 on mounting post 32 is screwed tight against the underside of fixator 12, thereby holding rotator 60 in place and thereby maintaining the desired tension in affixation wire 14.

Figure 9A:
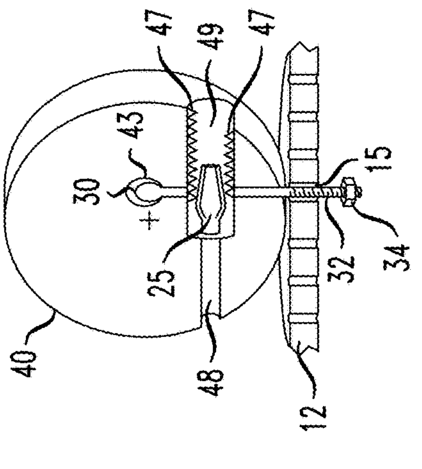
FIGS. 9A-9B are partial cross-sectional perspective views of another illustrative wire fixation device embodying the principles of the invention, the views depicting the wire fixation device at different stages of a method performed by a surgeon using the wire fixation device to tension and secure a bone-fixation wire onto a fixator.
Figure 9B:
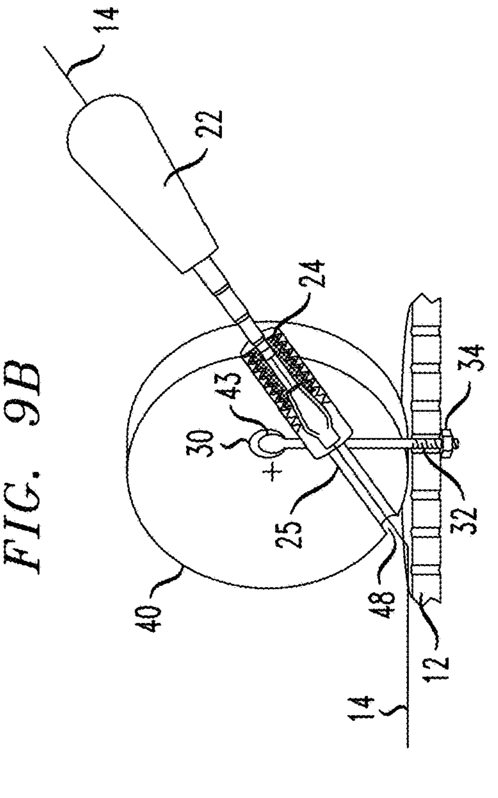

Also shown in FIGS. 9A-9B is that in this embodiment wire 14 is secured within rotator 40 using the same approach used in the embodiment of FIGS. 4A-4D employing cannulated nut 21 that, when screwed into channel 49, squeezes together the leafs 25*a* of collet 25 which, in turn, grab onto wire 14 and secure it within the rotator.

The elements of this embodiment correspond generally to those in the embodiments of FIGS. 4A-4D and FIGS. 8A-8D and thus comprise rotator 40; channel 48; channel 49 having within it collet 25 and having threads 47 on the channel wall; a mount comprising hub 30, threaded mounting post 32 that will be extended through hole 15 of fixator 12 when the wire fixation device is being put in place on fixator 12, and nut 34 threaded onto mounting post 32. Hub 30 extends through hole 43 in rotator 40, whereby rotator 40 is rotatable around hub 30 to the position shown in FIG. 9B.

Also shown in FIGS. 9A-9B is that in this embodiment wire 14 is secured within rotator 40 using the same approach used in the embodiment of FIGS. 4A-4D employing cannulated nut 24 that, when screwed into channel 49, squeezes together the leafs 25*a* of collet 25 which, in turn, grab onto wire 14 and secure it within the rotator.

It will be recalled that in the embodiments of FIGS. 4A-4D and 8A-8D, hub 30 is substantially in the center of rotator 20. A notable difference between the embodiment of FIGS. 9A-9B and that of FIGS. 4A-4D and 8A-8D is that in the former, hub 30 is offset from the center of rotator 40, which is demarcated with a "+" in FIGS. 9A and 9B to make this distinction easier to visualize. The purpose of having hub 30 offset from the center of rotator 40 is to facilitate securing the rotator tightly once it is in its rotated position. In practice, what the surgeon may do is put nut 34 in a somewhat snug position vis-à-vis the underside of fixator 12 and initiate the rotation. There will typically be at least some "give" or "play" of hub 30 within hole 43. Because of the offset, the rotation of rotator 40 will have the effect of pushing hub 30 toward the top of hole 43, thereby engendering increasing force between rotator 40 and fixator 12 and between hub 30 and the inside of hole 43 as the rotation progresses toward the final position of rotator 40 shown in FIG. 9B. If rotation is accomplishable, the surgeon may sense by feel that the fixation could be even tighter and so s/he may back off the rotation, then tighten nut 34 a little bit and then attempt rotation again, this process being repeated until the tightest position of nut 34 that still allows for rotation is found, thereby providing an optimal or near-optimal position of nut 34 as regards the tightness with which rotator 40 is held in place.

The ultimate result of this approach is that the surgeon may be able to more readily and/or quickly achieve the maximum achievable fixation of rotational element 40 in its final rotated position (FIG. 9B) than might be achieved in the embodiment of FIGS. 4A-4D and 8A-8D which relies solely on being able to maximally tighten nut 34 against the underside of fixator 12.

Figure 10A:
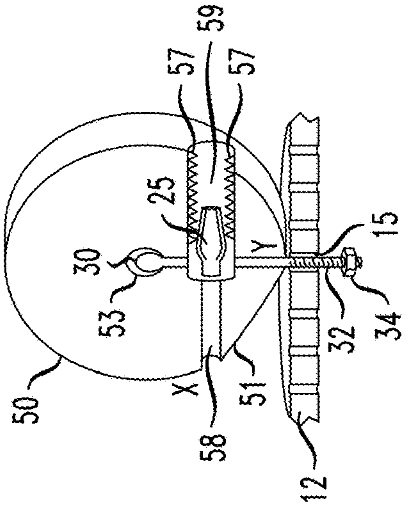
FIGS. 10A-10B are partial cross-sectional perspective views of another illustrative wire fixation device embodying the principles of the invention, the views depicting the wire fixation device at different stages of a method performed by a surgeon using the wire fixation device to tension and secure a bone-fixation wire onto a fixator.
Figure 10B:
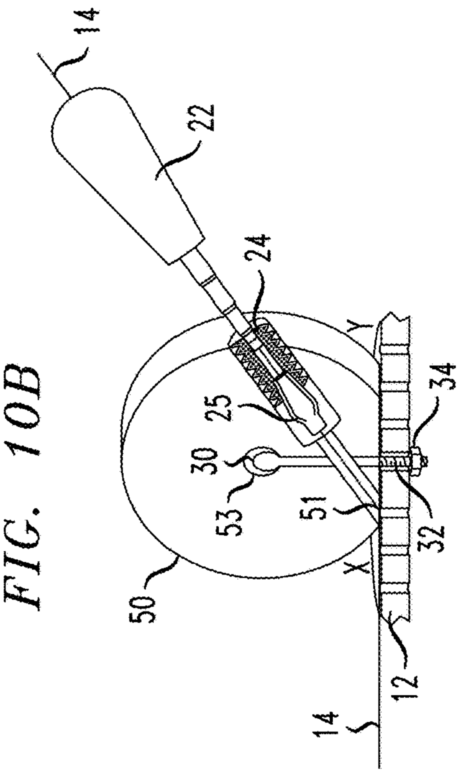

FIGS. 10A-10B are cross-sectional perspective views of another illustrative wire fixation device embodying the principles of the invention, the views depicting the wire fixation device at different stages of a method performed by a surgeon using the wire fixation device to tension and secure a bone-fixation wire onto a fixator. The elements of this embodiment correspond generally to those in previously described embodiments and thus comprise rotator 50; channel 58; channel 59 having within it collet 25 and having threads 57 on the channel wall; a mount comprising hub 30, threaded mounting post 32 that will be extended through hole 15 of fixator 12 when the wire fixation device is being put in place on fixator 12, and nut 34 threaded onto mounting post 32. Hub 30 extends through hole 53 in rotator 50, whereby rotator 50 is rotatable around hub 30. As previously, wire 14 is secured within rotator 50 using cannulated nut 21 and collet 25.

As in the embodiments of FIGS. 4A-4D and 8A-8D, hub 30 is substantially in the center of rotator 50. A difference here is that the external surface of rotator 50 has a region 51 between points X and Y that has less curvature than the rest of the external surface of rotator 50. That is, region 51 is at least somewhat "flattened" relative to the rest of the external surface of rotator 50. Thus in this embodiment the side edge of rotator 60 is not totally circular, as in the previously described embodiments. The location of region 51 on rotator 50 is such that region 51 is brought into contact along the upper surface of fixator 12 upon rotation, as seen in FIG. 10B. Once nut 34 has been tightened after rotator 50 has been rotated to its rotated position, it will be very difficult for rotator 50 to be dislodged from that rotated position given the relative flatness of region 51, thereby providing potentially enhanced protection—as compared, for example, the embodiments of FIGS. 4A-4D and 8A-8D—against subsequent dislodgement of rotator 50 from its rotated position (FIG. 10B) and subsequent loss of tension in wire 14.

Variations of the embodiment of FIGS. 10A-10B include the possibility of region 51 bulging out from rotator 50 to a greater or lesser degree than shown in the drawing. Furthermore, the radius of curvature between points X and Y might vary across region 51. Another possibility is that region 51 might be a substantially flat plane rather than being a curved surface. Or instead of being a smooth curved surface, region 51 might comprise a sequence of flattened planes with either equal or varying dihedral angles between successive ones of the planes.

The approaches described hereinabove for securing the rotator can be combined. Thus, for example, hole 53 in the embodiment of FIGS. 10A-10B could be off-center as in the embodiment of FIGS. 9A-9B, Indeed, in the various embodiments already disclosed and those to be discussed, a) the hub could be off-center, b) the surface of the rotator could incorporate any of the above-discussed possibilities for a flattened region like region 51, or c) both of those In the embodiments described to this point, the rotator is mounted directly on the mount that comprises hub 30, mounting post 32 and nut 34. By contrast, the embodiments of FIGS. 11-13 have a different mounting scheme wherein the mount for the rotator is a non-rotatable element that, in these embodiments, is similar in size and shape to the rotator although it need not be. The non-rotatable element is the thing that's actually mounted on the fixator—illustratively using a mounting post and nut as in the previously-described embodiments.

Figure 11:
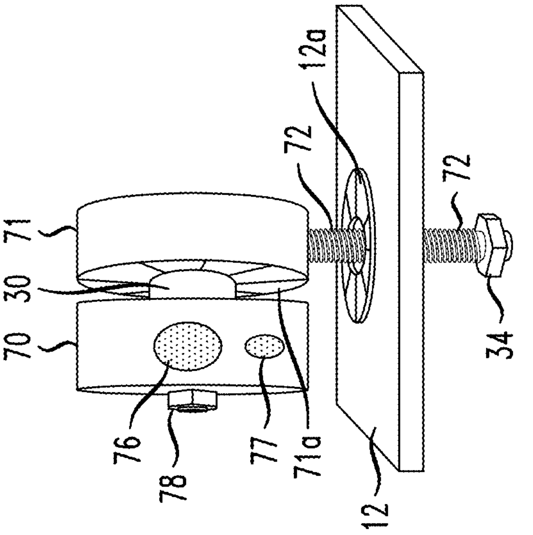

Referring in particular to FIG. 11, then, the wire fixation device includes rotator 70 having a channel 77 for the fixation wire (not shown) and a hole 76 to receive a tensioning lever to rotate the rotator. The tensioning lever could be a metal rod, a screwdriver or any other convenient device. The mount for rotator 70 comprises a) non-rotatable element 71 extending from which is hub 30 around which rotator 70 is rotatable and b) mounting post 72 and nut 34 affixed to non-rotatable element 71. In order to clearly show hub 30 in the FIG, rotator 70 and non-rotatable element 71 are shown in the FIG. to be spaced apart but would actually be disposed close to one another. Rotator 70 is illustratively held in place on hub 30 by a nut 78 tightened onto a threaded end portion (not shown) of hub 30. The wire fixation device is shown in its pre-tightened-down position wherein mounting post 72 has been passed through a hole in fixator 12 but the wire fixation device is not yet tightened against fixator 12 by nut 34.

As with the various embodiments disclosed herein, rotator 70 can be held in its desired rotated position using any or all of the various approaches described above, thus including a) the tightening of nut 34 which then brings both non-rotatable element 71 and rotator 70 into secure contact with fixator 12, b) having hub 30 be off center on rotator 70 and/or c) providing rotator 70 with a flattened region such as region 51 shown, for example, in FIGS. 10A-10B. This is also the case for the further embodiments described hereinbelow.

In addition, the fixation wire (not shown) that would be inserted through channel 77 can be secured within that channel using any of the mechanisms for doing that that are described hereinabove. This is also the case for the further embodiments described hereinbelow.

It should also be noted that in other embodiments the non-rotatable element 71 need not be similar in size and shape to the rotator. It only needs to be of a size and/or shape sufficient to securely hold hub 30.

Two factors—the tightening of nut 34 against the underside of fixator 20 and the fact that the wire itself will have been put under tension—may well be enough to ensure that the wire fixation device will not twist once secured in place. However, further insurance against such twisting can be had, per another feature of the wire fixation device of FIG. 11, by the presence of a serrated poker-chip-type surface 12*a* on the top surface of fixator 12 and a similar surface (not seen in the FIG.) on the bottom surface of non-rotatable element 71. Such serrated surfaces could be formed directly into fixator 12 and non-rotatable element 71 or they could be the surfaces of physically separate elements that are affixed to fixator 12 and non-rotatable element 71. Once the non-rotatable element 71 is secured on fixator 12, the opposing serrations will interlock and can serve as a mechanism to help ensure that the wire fixation device cannot twist. The presence of the serrations can also help prevent any movement of the wire fixation device laterally along fixator 12 in situations where the fixator has slots rather than holes through which the mounting post is inserted.

Such serrations could be provided in any of the embodiments previously described.

Figure 12:
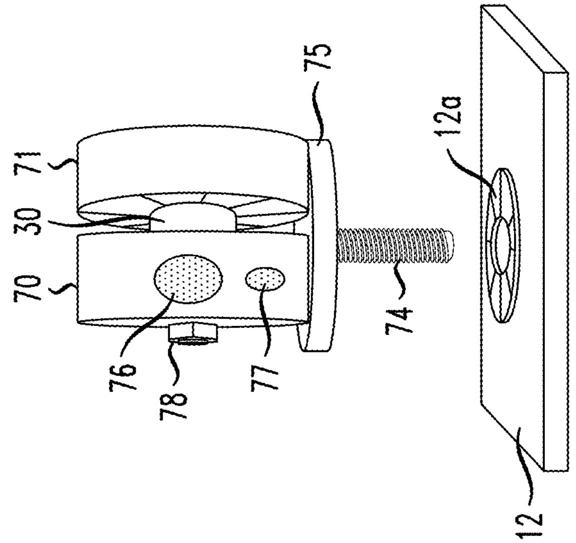
FIGS. 11-13 are side views of respective further illustrative wire fixation devices embodying the principles of the invention wherein a mounting post for securing the wire fixation device to a fixator extends from a non-rotatable element.

The embodiment of FIG. 12 includes a rotator and non-rotatable element similar to those in the embodiment of FIG. 11. A principal difference here is that the rotator 70 and non-rotatable element 71 sit on a platform 75 rather than directly on fixator 12 and, if serrations as described above are desired, such serrations can be present on the underside of platform 75. Since rotator 70 is secured in place by virtue of its contact with platform 75, the embodiment of FIG. 12, advantageously, is not limited to being mounted into a surface big enough for rotator 70 and non-rotatable element 71 to be mounted thereon. Rather, the wire fixation device of FIG. 12 can be mounted anywhere that there is a hole through which mounting post 74 can be inserted.

Figure 14:
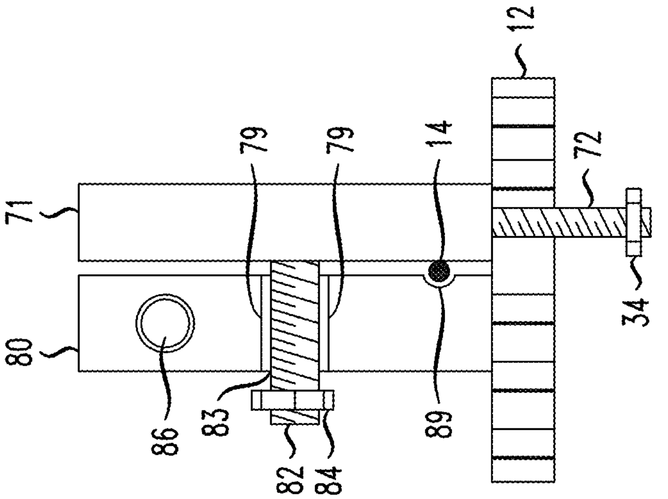
FIG. 14 is a cross-sectional view of another illustrative wire fixation device embodying the principles of the invention.
Figure 13:
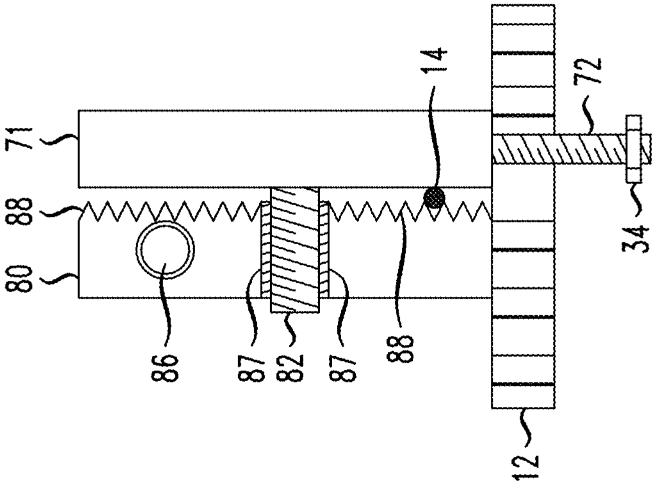

The embodiments of FIGS. 13 and 14 differ from those described above in that the fixation wire 14 is secured not within the rotator but, rather, on the rotator.

The embodiment of FIG. 13 includes rotator 80 mounted through hole 87 onto a hub 82 extending from non-rotatable element 71 which, in turn, is securable to fixator 12 by way of mounting post 72 and nut 34. Rotator 80 further includes a hole 86 into which can be inserted a tensioning lever for rotating the rotator.

In this embodiment, hub 82 and hole 87 are threaded, and so rotator 80 is put in place by turning it clockwise (as viewed from the left) after hub 82 has been inserted into hole 87. Rotator 80 is thereby moved increasingly close to non-rotatable element 71. Fixation wire 14 will be inserted between rotator 80 and non-rotatable element 71 after rotator 80 has gotten quite close to non-rotatable element 71 such that wire 14 will be captured by one of the sawteeth 88 that comprise the sawtoothed section of rotator 80 depicted in the FIG. Subsequent rotation of rotator 80 using the tensioning lever (not shown) that will have been inserted into hole 86 will squeeze wire 14 between rotator 80 and non-rotatable element 71, thereby securing wire 14 onto rotator 80 and at the same time tensioning wire 14.

The embodiment of FIG. 14 includes rotator 80 mounted through hole 79 onto a hub 83 extending from non-rotatable element 71 which, in turn, is securable to fixator 12 by way of mounting post 72 and nut 34. Rotator 80 includes hole 86 into which can be inserted a tensioning lever for rotating the rotator.

In this embodiment, hub 83 is threaded at least at its free end and hole 79 on which hub 83 is mounted is not threaded. Fixation wire 14 will be inserted into a half-pipe-type channel 89 on the outside surface of rotator 80 at which point a nut 84 is threaded onto hub 83 and tightened against rotator 80, bringing rotator 80 and non-rotatable element 71 as close together as will be possible given the presence of wire 14 whose diameter is greater than the radius of channel 89. Wire 14 is thereby secured onto rotator 80. Subsequent rotation of rotator 80 using a tensioning lever (not shown) that will have been inserted into hole 86 will tension wire 14. As an alternative to using nut 84 to hold rotator 80 in place, both hole 79 and hub 83 can be threaded so that rotator 80 can be screwed on to hub 83.

Figure 15A:
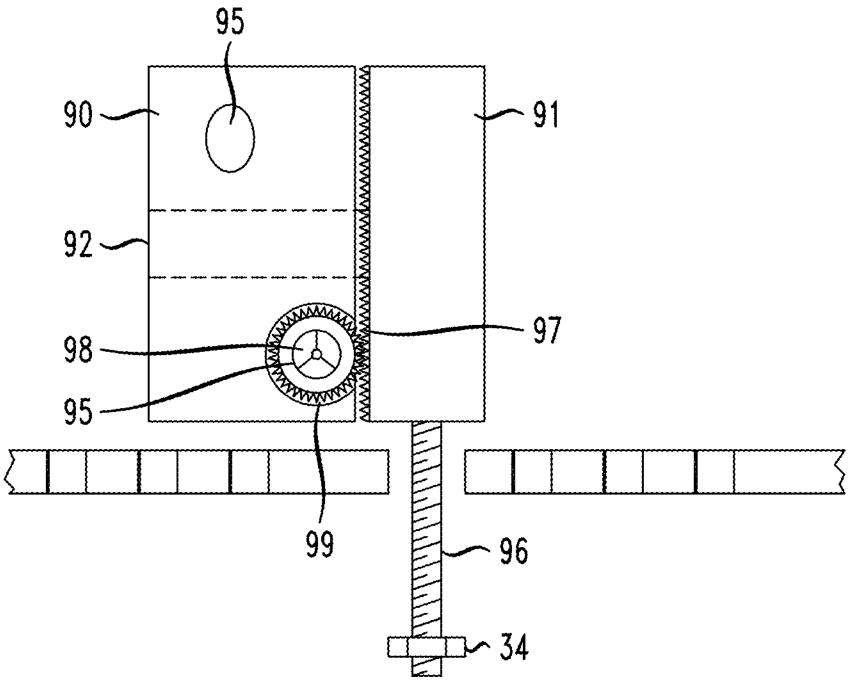
FIGS. 15A and 15B are, respectively, front, and top views of a further embodiment of the invention.
Figure 15B:
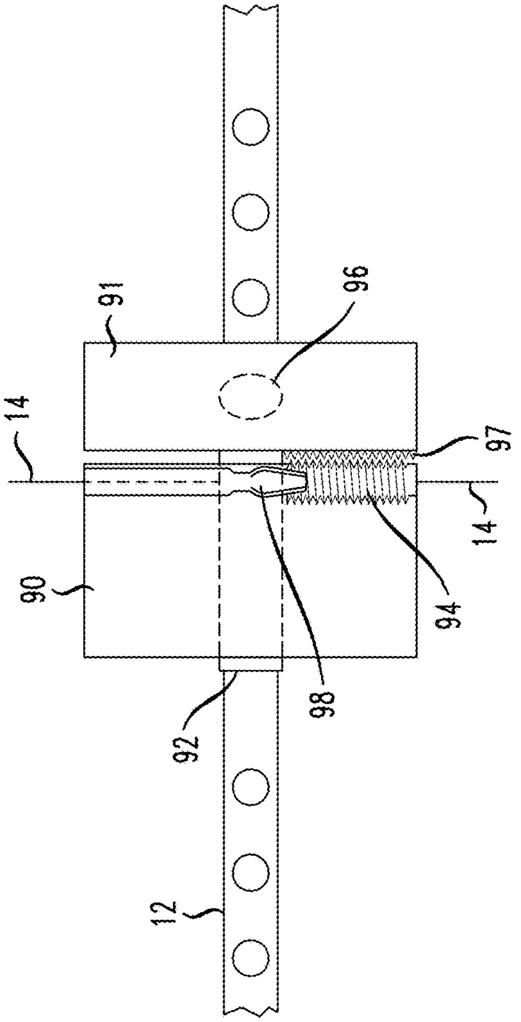
Figure 15C:
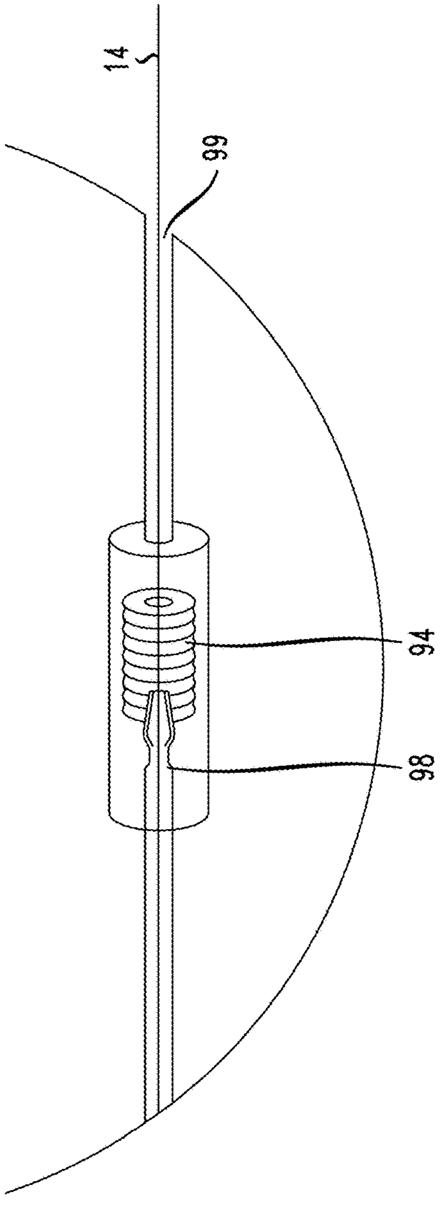
FIG. 15C is a side view showing an internal detail of the embodiment of FIGS. 15A-15B.

FIGS. 15A-15C are, respectively, perspective, front, and top views of a further embodiment of the invention.

The wire fixation device of this embodiment includes rotator 90 mounted on, and rotatable around, a hub 92 extending from non-rotatable element 91 which, in turn, is affixable to fixator 12 by way of mounting post 96 passed through a hole in fixator 12 and secured with nut 34. A hole 95 is provided to receive a tensioning lever (not shown) to facilitate the rotation of rotator 90 to its rotated position.

A channel 99 extends through rotator 90 and disposed within channel 99 is a cannulated nut 94 and a collet 98 which are aligned coaxially within channel 99 with the tip of collet 98 being just outside of cannulated nut 94. The leafs of collet 98 are thus initially in their spread-apart configuration, allowing wire 14 to be passed into channel 99, through collet 98 and cannulated nut 94, and then continuing through channel 99 and out the other side of rotator 90.

Cannulated nut 94 is disposed in such a way that its exterior threads extend beyond the inner surface of rotator 90 so as to engage with ribs 97 on the inner surface of non-rotatable element 91. Ribs 97 are angled in such a way as to fit into the valleys of the screw threads of cannulated nut 94. As a result, when rotator 90 is thereupon rotated to its rotated position, the engagement of ribs 97 with the exterior threads of cannulated nut 94 rotates the nut and at the same time advances it along channel 99 in the direction of collet 98 so that the leafs of the collet are entered into the cannula of nut 94 and are thereby squeezed together so as to grip onto and secure wire 14. The rotation of rotator 90 thus serves the dual purpose of securing wire 14 within the rotator and tensioning it.

Like the embodiment of FIGS. 15A-15C as just described, the embodiment of FIGS. 16A-16E has the feature that it is the rotation of the rotator that causes wire 14 to become secured within the rotator, but by a different mechanism.

Figure 16A:
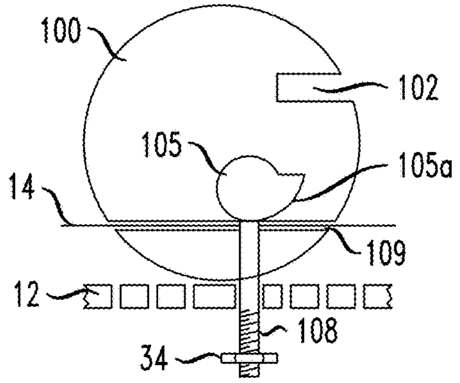
FIGS. 16A-16C are partial cross-sectional views of another wire fixation device embodying the principles of the invention, the various views depicting the wire fixation device at different stages of a method performed by a surgeon using the wire fixation device to tension and secure a bone-fixation wire onto a fixator.

Specifically, and with reference to FIG. 16A, rotator 100 of this embodiment is directly mountable onto the fixator 12, this being achievable, as in previously described embodiments, by virtue of the rotator being secured on a mount that comprises a hub 105, mounting post 108 and nut 34. That is, in this embodiment the mount does not include the non-rotatable element featured in some of the previously described embodiments although other versions of this wire fixation device could be mounted on that latter type of mount. Channel 109 extends through rotator 100 and wire 14 is extended through the channel as shown.

A unique feature of this embodiment is that the top of channel 109 has an open region into which hub 105 protrudes to some extent and moreover hub 105 differs from the hubs used in the previously described embodiments in that its cross-section is not circular. Rather, hub 105 is cam-like in that it has a projection, or "ramp," 105*a*.

Figure 16B:
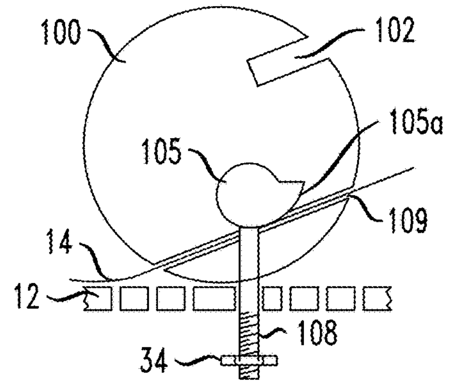
Figure 16C:
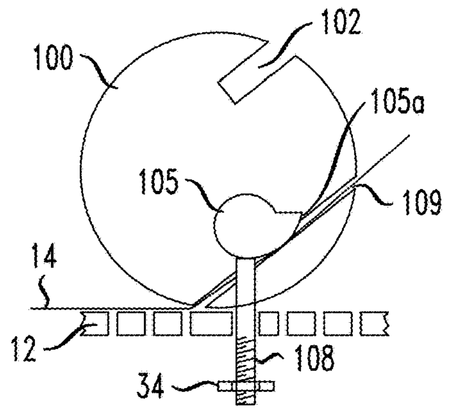
Figure 16D:
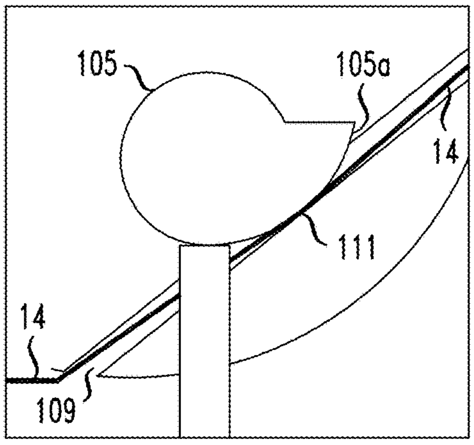
FIG. 16D is a magnified view of a portion of the embodiment at the point in time depicted in FIG. 16C.
Figure 16E:
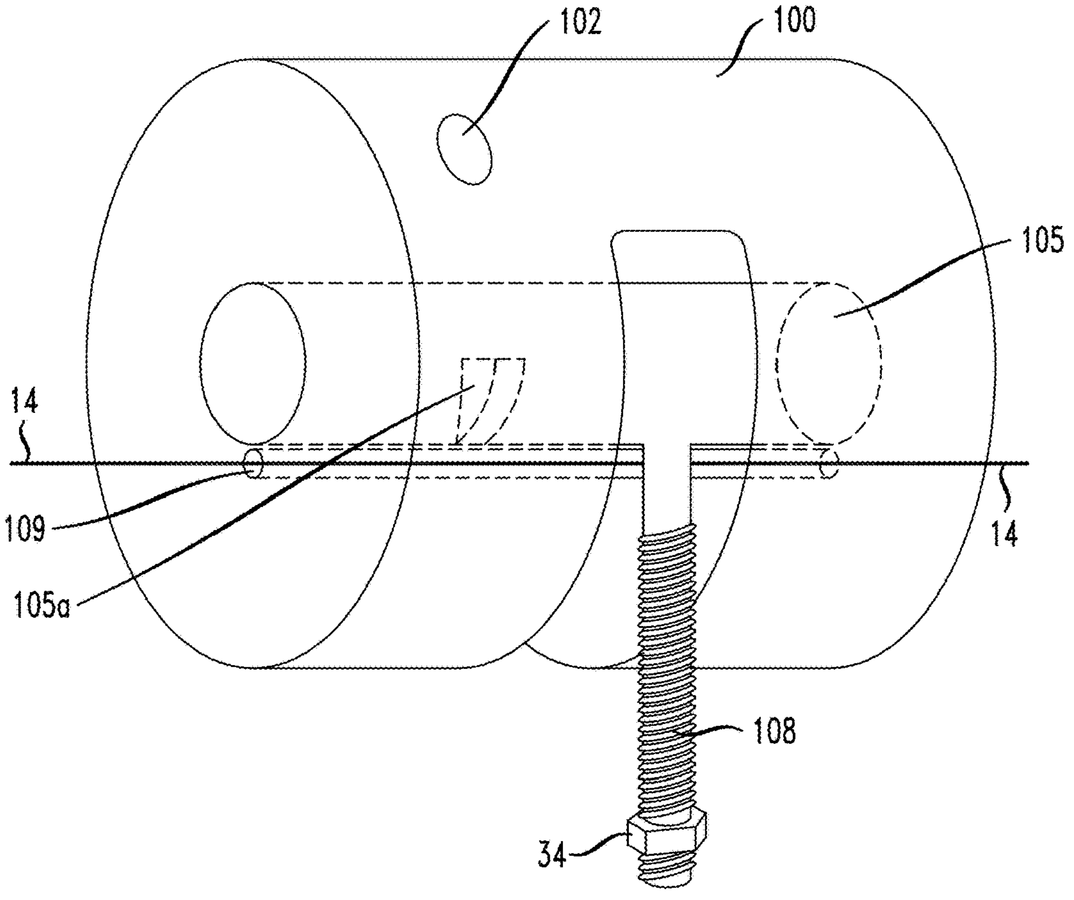
FIG. 16E is a perspective view of the embodiment of FIGS. 16A-16D.

Referring now to FIG. 16B, when a tensioning lever (not shown) is inserted into hole 102 and is used to rotate the rotator, ramp portion 105*a* of hub 105 begins to be the portion of hub 105 that protrudes into channel 109, thereby beginning to close down the space between hub 105 and wire 14. And at the point in time when rotator 100 has been rotated into its fully rotated position, as shown in FIG. 16C, ramp 105*a* will have completely closed down the space between hub 105 and wire 14, thereby trapping wire 14 against the side of channel 109 and securing it within the rotator, as shown in detail at 111 in FIG. 16D.

A significant advantage of this embodiment is that it requires fewer parts than other embodiments and avoids the need for certain intermediate steps that are involved in others of the embodiments, such as the need to insert and screw into place a separate part such as cannulated nuts 24 and 64 used in others of the disclosed embodiments.

Figure 17:
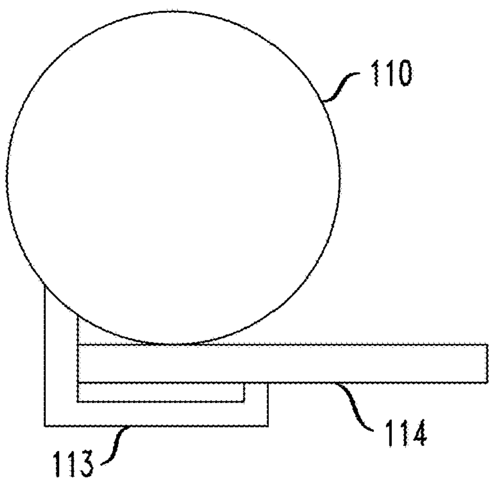
FIG. 17 shows an alternative way of securing wire fixation devices of the present invention to a fixator.

FIG. 17 shows an alternative way to secure the wire fixation device to the fixator. Instead of using a threaded mounting post, a bracket 113 is attached to a non-rotatable element such as those shown in FIGS. 11-14. The bracket wraps around the outside rim of fixator 114 which differs from fixator 12 in that it does not have to have any holes. As the bone-fixation wire (not shown) is put under tension, the vertical leg of backet 113 is pulled tight against the outside rim of fixator which may have a lip or may have indents, or concavities, spaced along the rim into which the bracket can fit and thus be prevented from being displaced.

Figure 18:
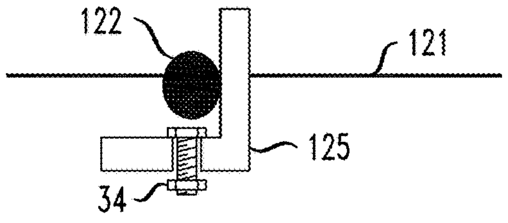
FIG. 18 shows an alternative way of affixing to a fixator the end of a bone-fixation wire opposite from the end that is secured with a wire fixation device of the present invention.

FIG. 18 shows an alternative way to the secure bone-fixation wire to the fixator at the location opposite to the wire fixation device. L-shaped bracket 125 can be attached to the fixator at that location. A ball, or stopper, 122 is permanently secured to wire 121 and the wire is held in a slot (not shown) in bracket 125. As the wire is tightened the ball is pulled tight against the inside wall of the bracket.

Possible variations applicable to various ones of the disclosed embodiments may use a number of spaced-apart ball bearings instead of, say, a collet, arranged circularly within a rotator's channel. The bone-fixation wire would be passed through the circle of ball bearings. One of various mechanisms could be provided to push the ball bearings inwardly to thus grab and secure the bone-fixation wire in a way corresponding to the way in which the collet leafs of other embodiments are pushed together to grasp onto and secure the wire.

In other embodiments, the rotator may comprise upper and lower sections that are held spaced apart by some form of linkage and the bone-fixation wire is passed between the two sections. A tensioning lever would be used to rotate the top section. The wire tensioning device is so arranged that upon rotation of the upper section, the lower section is caused to be urged against the upper section, thereby grabbing and securing the wire.

Yet a further possible variation applicable to all of the disclosed embodiments is the manner in which the wire fixation device and, in particular, the mounting post, is secured onto fixator 12. Instead of the mounting post being threaded and receiving nut 34 to tighten the wire fixation device onto fixator 12, the mounting post may feature an arrangement known as a ball pin lock wherein two or more ball bearings are disposed within a distal end of the mounting post but extending to somewhat outward positions beyond the mounting post surface. A spring or similar mechanism inside the mounting post will bias the ball bearings to occupy those outward positions. But the ball bearings are moveable to respective inner positions toward a longitudinal axis of the post. Thus when the mounting post is positioned over a hole on the fixator, and the wire fixation device is pushed down, the ball bearings are pushed to positions of retreat into the post, allowing the post to pass into the hole. Once the ball bearings clear the hole, they then spring back to occupy their original outward positions. The position of the ball bearings along the mounting post is such that when the ball bearings spring back to occupy their original outward positions, they will be directly under, and in close contact with, the underside of the fixator, thereby holding the wire fixation device securely on the fixator.

Typical dimensions for various parts of the wire fixation device may be, for channels 8 and 9, a length of approximately between 3 mm and 10 mm and a diameter of between 1 mm and 10 mm. The overall diameter of the rotator may be approximately between 10 mm and 30 mm and its thickness may be approximately between 8 mm and 20 mm. Other parts of the wire fixation device will be sized consistent with these. Typical materials out of which the various components of the disclosed wire fixation devices may be fabricated include, but not limited to, metals such as surgical steel or aluminum, radiolucent plastics, carbon fiber or a combination of these or other materials.

The present invention further comprises methods of tensioning a bone-fixation wire, wherein the tensioning is carried out using the inventive wire fixation device. Thus the steps of an illustrative method embodying the principles of the invention comprise affixing a first portion of wire 14 at a first location on fixator 12, affixing a second portion of the wire at a second location on the external bone fixator using a wire fixation device embodying the principles of the invention as described herein, and manipulating the wire fixation device as described herein in such a way as to tension the wire and to secure the wire in its tensioned state. If desired, wire fixation devices embodying the principles of the invention could be used to affix the wire at both locations on the fixator.

Modifications, additions, or omissions may be made to the systems, apparatuses, and methods described herein without departing from the scope of the invention, and are expressly contemplated herein. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order.

Other embodiments of the invention will be apparent to those skilled in the art from consideration of the specification.

Thus, for example, wire 14 could be secured on a rotator with, say, a set screw or clip, just to mention two possibilities, as alternatives to the embodiments of FIGS. 13 and 14. In addition, a clip or other device could be used in place of nut 34 to secure the wire fixation device to the fixator.

Moreover, although specific advantages have been enumerated above, various embodiments may include some, none, or all of the enumerated advantages. It is intended that the embodiments described above be considered as exemplary only. In addition, it should be understood that any of the features disclosed on any particular embodiment may be incorporated in whole or in part on any of the other disclosed embodiments.

In general, combinations of numerous ones of the disclosed features, components and methods described herein are possible. Steps of a method can be performed in any order that is physically possible.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description hereinbelow.

Any cited references are incorporated by reference herein in their entirety.

The invention claimed is:

1. A wire tensioner fixation device for use with a substantially planar external bone fixator, the external bone fixator being in the form of a substantially planar ring or ring segment, the wire tensioner fixation device comprising a mount adapted to be extended through the external bone fixator, and a disc-shaped rotator that a) is affixed to the mount, b) is rotatable with respect to the mount in a direction substantially non-paralleling the plane of the substantially planar external bone fixator, and c) includes at least one wire-engaging element that enables the rotator to secure a bone-fixation wire in or on the rotator.

2. The wire tensioner fixation device of claim 1 wherein when a distal end of the bone-fixation wire is secured to the fixator, subsequent rotation of the rotator tensions the bone-fixation wire.

3. The wire tensioner fixation device of claim 1 wherein the rotator is configured in such a way as to become secured at a second position when rotated from an initial position to that second position, with the bone-fixation wire being in a tensioned state.

4. The wire tensioner fixation device of claim 1 wherein the rotator has a channel within, and extending through, the rotator and wherein the at least one wire-engaging element is disposed within the channel.

5. The wire tensioner fixation device of claim 1 wherein the at least one wire-engaging mechanism comprises a collet.

6. The wire tensioner fixation device of claim 5 wherein the collet includes a plurality of leafs operable to grasp the bone-fixation wire.

7. The wire tensioner fixation device of claim 1 wherein the wire-engaging element and the mount are adapted to secure the bone-fixation wire against the mount.

8. The wire tensioner fixation device of claim 1 wherein the mount includes a hub and wherein the rotator is rotatable around the hub.

9. The wire tensioner fixation device of claim 1 wherein the rotator has a channel that is within the rotator and that extends through the rotator and wherein the wire-engaging element is a projection on the hub that is configured to increasingly extend into the channel as the rotator is rotated and thereby secure the bone-fixation wire against the inside of the channel.

10. The wire tensioner fixation device of claim 8 wherein the rotator has a center around which it is rotatable and wherein the hub is at other than said center of the rotator.

11. The wire tensioner fixation device of claim 8 wherein the rotator is non-circular.

12. The wire tensioner fixation device of claim 11 wherein the non-circular rotator has at least a first edge section having less curvature than at least a second edge section of the rotator.

13. The wire tensioner fixation device of claim 12 wherein one or both of the rotator and the mount are so arranged as to enable the rotator to be secured at a rotated position at which the first edge section is against the external bone fixator.

14. The wire tensioner fixation device of claim 1 wherein one or both of the rotator and the mount are so arranged as to enable the rotator to be secured at a rotated position.

15. The wire tensioner fixation device of claim 1 wherein the mount includes a mounting post adapted to be inserted through a hole in the external bone fixator and wherein the mounting post has external threads for receiving a threaded fastener.

16. The wire tensioner fixation device of claim 1 wherein the mount includes a bracket adapted to hook onto a rim of the external bone fixator.

17. The wire tensioner fixation device of claim 1 wherein the rotator is adapted to accept a tensioning lever to which force can be applied to rotate the rotator.

18. Apparatus comprising a wire tensioner fixation device and a substantially planar external bone fixator in the form of a substantially planar ring or ring segment, wherein the wire tensioner fixation device comprises a) a mount extended through the external bone fixator, and b) a disc-shaped rotator that a) is affixed to the mount, b) is rotatable with respect to the mount in a direction substantially non-paralleling the plane of the substantially planar external bone fixator, and c) includes at least one wire-engaging element that enables the rotator to secure a bone-fixation wire.

19. A method comprising affixing a first portion of a bone-fixation wire at a first location on a substantially planar external bone fixator, the external bone fixator being in the form of a substantially planar ring or ring segment, affixing a second portion of the wire at a second location on the external bone fixator using a wire tensioner fixation device which comprises a mount extended through the external bone fixator, and a disc-shaped rotator that a) is affixed to the mount, b) is rotatable with respect to the mount in a direction substantially non-paralleling the plane of the substantially planar external bone fixator, and c) includes at least one wire-engaging element that enables the rotator to secure a bone-fixation wire in or on the rotator, and rotating the wire tensioner fixation device in such a way as to tension the wire and to secure the wire in a tensioned state.

20. The wire tensioning device of claim 1 wherein at least a portion of the mount is a mounting post securable substantially perpendicularly to the external bone fixator.

21. The apparatus of claim 18 wherein at least a portion of the mount is a mounting post secured substantially perpendicularly to the external bone fixator.

22. The method of claim 19 wherein at least a portion of the mount is a mounting post that is secured substantially perpendicularly to the external bone fixator.

23. The wire tensioning device of claim 1 wherein the wire-engaging element is enclosed within a channel that extends into the interior of the rotator.

24. The apparatus of claim 18 wherein the wire-engaging element is enclosed within a channel that extends into the interior of the rotator.

25. The method of claim 19 wherein the wire-engaging element is enclosed within a channel that extends into the interior of the rotator.

* * * * *